United States Patent
Patel et al.

(10) Patent No.: US 6,411,836 B1
(45) Date of Patent: Jun. 25, 2002

(54) METHOD AND APPARATUS FOR USER PREFERENCES CONFIGURING IN AN IMAGE HANDLING SYSTEM

(75) Inventors: Alpesh P. Patel, Schaumburg; Roland Lamer, Evanston, both of IL (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 09/475,522

(22) Filed: Dec. 30, 1999

(51) Int. Cl.[7] ................................................. A61B 5/05
(52) U.S. Cl. ...................................................... 600/407
(58) Field of Search ................................. 600/407; 705/3

(56) References Cited

U.S. PATENT DOCUMENTS 5,734,915 A * 3/1998 Roewer
6,117,079 A * 9/2000 Brackett et al.
6,125,350 A * 9/2000 Dirbas
6,260,021 B1 * 7/2001 Wong et al.

* cited by examiner

*Primary Examiner*—Marvin M. Lateef
*Assistant Examiner*—Runa Shah Qaderi
(74) *Attorney, Agent, or Firm*—Foley & Lardner; Peter J. Vogel; Michael A. Della Penna

(57) ABSTRACT

An image handling system configured to provide configurable user preferences is disclosed herein. The image handling system includes an imaging device, an image manager, and an image workstation. The system is configured to permit a user of the image workstation to specify user preferences of a graphical user interface (GUI). The user preferences are stored in the image manager such that subsequent access to the image workstation using a user identifier causes the image workstation to automatically retrieve and configure the user preferences on that image workstation.

30 Claims, 3 Drawing Sheets

METHOD AND APPARATUS FOR USER PREFERENCES CONFIGURING IN AN IMAGE HANDLING SYSTEM

BACKGROUND OF THE INVENTION

The present invention relates generally to image handling systems. More particularly, the present invention relates to an image handling system capable of providing configurable user preferences.

Presently in a hospital, medical imaging devices are preferably networked with a central image management system, such as a picture archival and communications system (PACS). Medical imaging devices utilize, among others, electromagnetic radiation, x-rays, sonic waves, and photonic energy to produce images of a subject of interest, such as a patient, to aid in examination and treatment. For example, ultrasound devices are useful for viewing fetuses during prenatal care in a pregnancy. Magnetic resonance (MR) imaging systems can produce images of a wide range of tissues.

The central image management system includes a central storage unit coupled to a plurality of image workstations or terminals, such as PACS workstations. The central storage unit is configured to archive images produced by the plurality of medical imaging devices, and to retrieve images for display on one or more image workstations. Thus, the hospital can provide a plurality of medical imaging devices located throughout the hospital, and images produced from any of these medical imaging devices can then be retrieved and viewed by physicians located throughout the hospital at any of the plurality of image workstations.

Presently, when a physician or other user accesses an image workstation, the user is able to retrieve images relating to one or more examinations (i.e., a set of images of a given patient for a particular examination) and the corresponding patient information. At the image workstation, the user is permitted to manipulate the images, such as zooming in on a portion of an image or changing the viewing order of the set of images. The user can also move between a plurality of work files, such as his all priority examinations, all unread examinations, all recent examinations, etc. In order to facilitate such navigation through the image sets, the image workstation includes a graphical user interface (GUI). The user can also specify his preferences in the layout and icons comprising the GUI during his session on the image workstation. However, as soon as the user ends his session (i.e., logs out) at that image workstation, all of his preferences are lost. Thus, even if he logs back onto the same image workstation, or to any other image workstation, all of his preferences would have to be reentered.

Thus, there is a need for an image management system capable of preserving users' preferences specified in image workstations. There is a further need for an image management system capable of automatically configuring the image workstation with the user's preferences in future sessions.

BRIEF SUMMARY OF THE INVENTION

One embodiment of the invention relates to a method of providing configurable user preferences in an image handling system. The method includes specifying user preferences relating to images in an image workstation. The method further includes storing the user preferences in an image manager. The user preferences are associated with a user identifier. The method still further includes configuring the image workstation with the user preferences selectively retrieved from the image manager. The configuring occurring in response to the user identifier information inputted to the image workstation for a subsequent session on the image workstation.

Another embodiment of the invention relates a medical image handling system. The system includes a medical imaging device configured to acquire an image of a subject of interest and represent the image in an image data set. The system further includes an image manager coupled to the imaging device. The image manager is configured to store user preferences communicated by an image workstation and the image data set communicated by the imaging device. The system still further includes the image workstation coupled to the image manager. The image workstation is configured to selectively retrieve the user preferences and the image data set from the image manager. The image workstation automatically configures a graphical user interface (GUI) to incorporate the user preferences based in part on a user identifier information inputted into the image workstation.

Still another embodiment of the invention relates to an image handling system. The system includes means for acquiring an image of a subject of interest, and means for representing the image in an image data set. The system further includes means for storing user preferences communicated by an image workstation and the image data set communicated by the means for acquiring and representing. The means for storing is coupled to the means for acquiring and representing. The system still further includes means for selectively retrieving the user preferences and the image data set from the means for storing. The image workstation automatically configures a graphical user interface (GUI) to incorporate the user preferences based in part on a user identifier information inputted into the image workstation. The means for selectively retrieving is coupled to the means for storing.

BRIEF DESCRIPTION OF THE DRAWINGS

The preferred embodiment will become more fully understood from the following detailed description, taken in conjunction with the accompanying drawings, wherein like reference numerals denote like elements, in which.

DETAILED DESCRIPTION OF THE INVENTION

Figure 1:
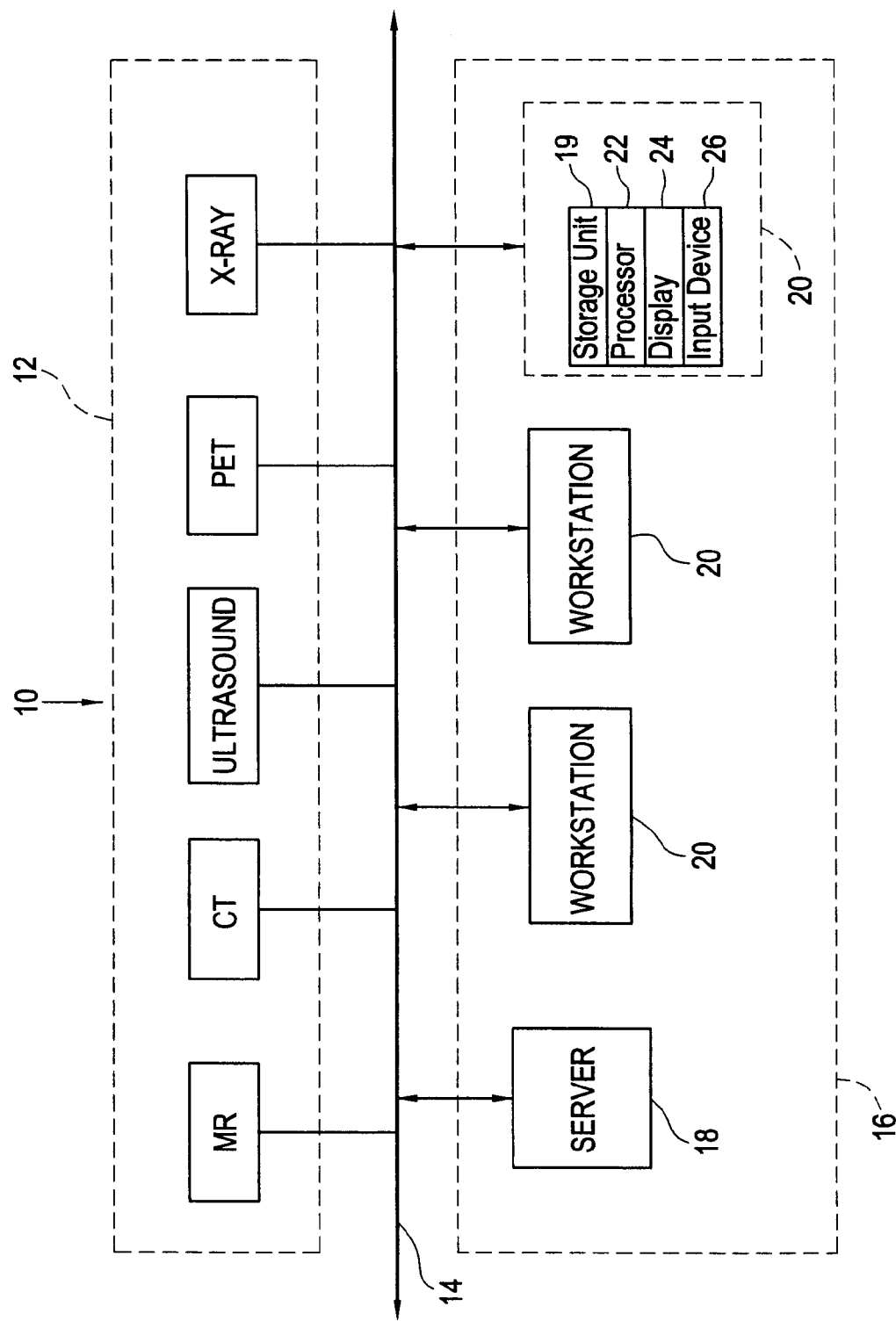
FIG. 1 is a block diagram of an image handling system which employs an embodiment of the present invention.

Referring to FIG. 1, there is shown the major components of an image handling system 10. Image handling system 10 includes imaging devices 12, a communications network 14, and an image management system 16. Each of the imaging devices 12 is coupled to the communications network 14 and the communications network 14 is coupled to the image management system 16.

Imaging devices 12 include, but are not limited to, magnetic resonance (MR) imaging devices, computerized tomography (CT) devices, ultrasound devices, nuclear imaging devices, x-ray devices, and a variety of other types of imaging devices. It should be understood that imaging devices 12 are not limited to medical imaging devices and can also include scanners and imaging devices from other fields. Imaging devices 12 are located throughout a facility, such as a hospital.

Image management system 16 includes an image manager 18 and a plurality of image workstations 20. Preferably, image management system 16 is a picture archival and communication system (PACS), image manager 18 is a PACS server, and the plurality of image workstations 20 are PACS workstations or terminals. It should be understood, however, that image management system 16 can be any image archival, management, and retrieval apparatus.

Image manager 18 includes an information storage unit for short-term storage and retrieval, and an archival storage unit (e.g., an optical disc storage and optical disc reader system) for long-term storage and retrieval (not shown). Each of the plurality of workstations 20 is a computer system or terminal, including a storage unit 19, a processor 22, a display 24, and an input device 26. Input device 26 can include, but is not limited to, a mouse, a joystick, a keyboard, a trackball, a touch screen, a light wand, and a voice control. Image manager 18 is coupled to each of imaging devices 12 and the plurality of workstations 20, via communications network 14 (e.g., an ether net, fiber optic, or other applicable communications network communication). The plurality of workstations 20 can be located throughout the hospital and need not be proximate imaging devices 12 or image manager 18.

During an examination of a subject of interest, such as a portion of a patient's anatomy, one or more imaging devices 12 are used to acquire images of the subject of interest. Each acquired image is in a digitized data format, preferably in a DICOM, DEFF, or other suitable format, and is communicated from imaging devices 12 to image manager 18 via communications network 14. Image manager 18 archives each image data set representative of one acquired image, also referred to as an image file, with appropriate identifiers and links such that the image file can be selectively retrieved. Once image files have been archived in image manager 18, Himage files and other relevant information, such as the patient's medical history, can be selectively retrieved and accessed on any one of the plurality of workstations 20 or other information retrieval devices coupled to communications network 14.

In one embodiment, each of the plurality of workstations 20 includes a graphical user interface (GUI) displayed on display 24. A user, such as a physician or radiologist, navigates the information retrieved from image manager 18 to workstation 20 via the GUI and input device 26. The GUI provides a logical and familiar environment in which the user can access, view, manipulate, and ultimately diagnose examinations which comprise his workload. To this end, the GUI is configured to include a worklist selector window 30 (see FIG. 2) and an image viewing window 40 (see FIG. 3).

Figure 2:
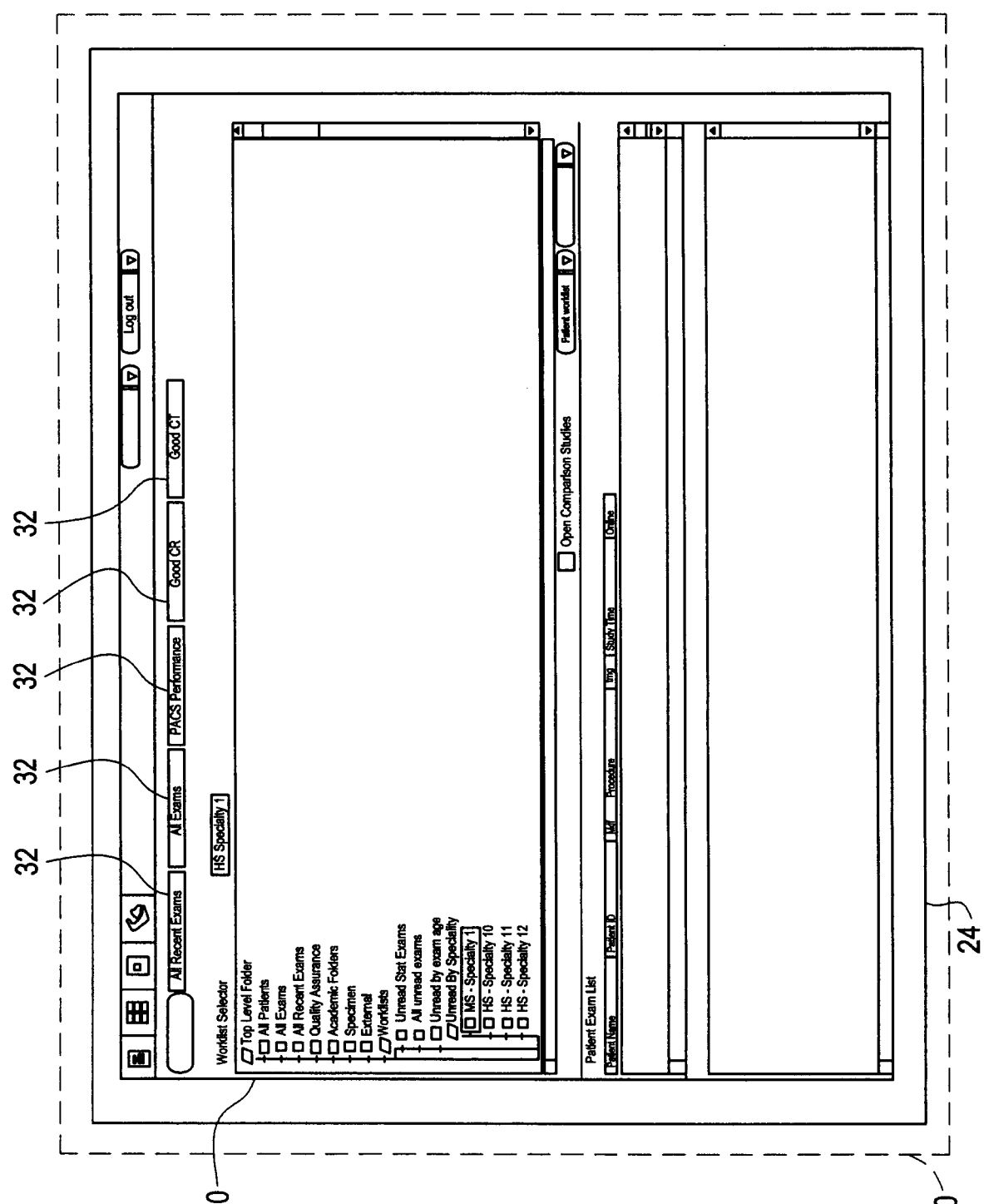
FIG. 2 is an illustration of a graphical user interface on a workstation which comprises a part of the image handling system of FIG. 1.

As shown in FIG. 2, worklist selector window 30 includes a plurality of icons to represent a variety of work files or categories of images, i.e., a worklist, that may be relevant to the user during his session on any one of the plurality of workstations 20. In other words, worklist selector window 30 is configured to provide indicia of a directory structure. The worklist icons can include, but is not limited to: an all patients icon, an all exams icon, an all recent exams icon, an unread stat exams icon, an all unread exams icon, an unread by exam age icon, an unread by specialty icon, a priority exams icon, and an academic folders icon. The user selects from any of the worklist icons to access the content associated therewith using input device 26.

Worklist selector window 30 further includes one or more quick access buttons or icons 32. Quick access icons 32 are preferably displayed on the top portion of window 30. Alternatively, a separate window may be implemented to display icons 32. Quick access icons 32 are configured by the user, i.e., specifically selected by the user from the worklist icons, using input device 26. For work files that the user repeatedly accesses, quick access icons 32 provide a convenient way to access these work files without having to navigate through the worklist icons. Once quick access icons 32 have been specified, they are made available to the user, in the worklist selector window 30, throughout his or her session on workstation 20. The user also has the option of changing the quick access icons 32 as often as desired.

Before the user ends his session on workstation 20, i.e., logs out of workstation 20, the quick access icons 32 are automatically saved as part of that user's permanent preferences in image manager 18. Alternatively, workstation 20 may explicitly require the user to save such quick access icons 32 before ending the session. Once the user's preferred quick access icons 32 have been saved in image manager 18, these preferred quick access icons 32 will always be configured for display on worklist selector window 30 when the user or anyone else using the user's login identifier starts a subsequent session, i.e., logs in, on any of the plurality of workstations 20.

Figure 3:
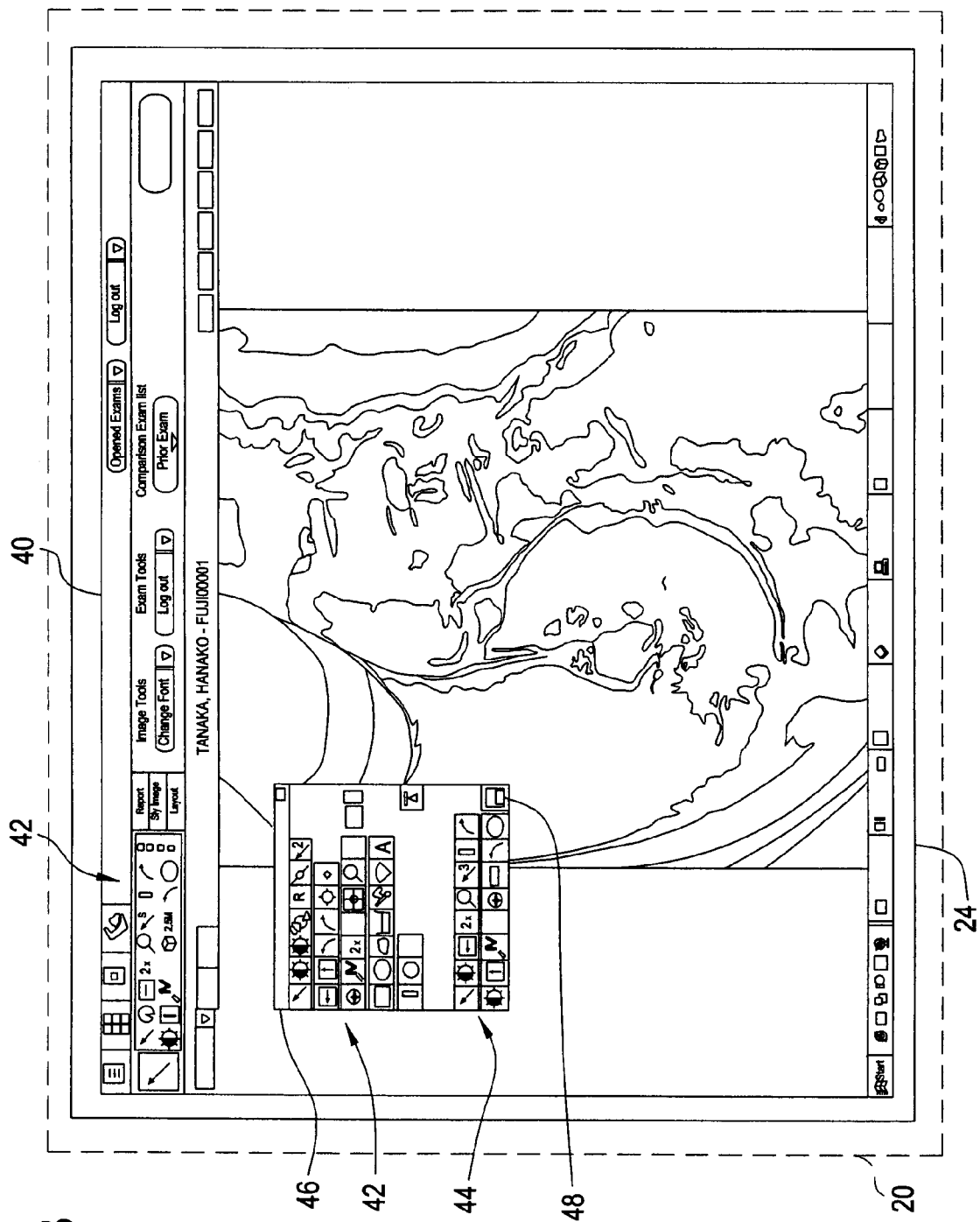
FIG. 3 is another illustration of a graphical user interface on the workstation which comprises a part of the image handling system of FIG. 1.

Referring to FIG. 3, there is shown the image viewing window 40 on which the user accesses, views, and manipulates one or more images downloaded from image manager 18. Window 40 includes a plurality of image tools icons 42 to permit the user to selectively view and manipulate images. Image tools icons 42 includes, but is not limited to: a magnify icon, a horizontal flip icon, a vertical flip icon, a pan icon, an image information icon, an invert grayscale icon, and an image mask icon.

Image viewing window 40 is further configured to permit the user to specify his preferred tool icons, i.e., user preferred buttons or icons 44, from among the plurality of image tools icons 42. As shown in FIG. 3, an extended tool palette window 46 can be implemented to display the plurality of image tools icons 42 on the top portion of window 46 and the user preferred icons 44 on the bottom portion of window 46. The user can update the user preferred icons 44 as many times as desired. Moreover, the user preferred icons 44 can be saved as a part of the user's permanent preferences in image manger 18 by "clicking" on a save icon 48. Alternatively, user preferred icons 44 may be saved automatically in image manager 18 at the end of the user's session on workstation 20. Then when the user or anyone else using the user's login identifier starts a subsequent session on any of the plurality of workstations 20, that user's preferences in the plurality of image tools icons 42 (i.e., represented by the saved user preferred icons 44) will automatically be communicated to that particular workstation 20 for display on image viewing window 40 and/or extended tool palette window 46.

Similarly, other user preferences such as a font preference or a font size preference may also be specified as part of the user's permanent preferences. If the user has no user preferences saved in image manager 18, the start of his session on any of the plurality of workstations 20 would be configured with default settings. Thus, each of a plurality of users can have his or her user preferences associated with his or her login identifier and have it saved in image manager 18. In this manner, any one of the plurality of workstations 20 will automatically configure and include a particular user's preferences when that particular user subsequently starts a session on that workstation.

While the embodiments illustrated in the figures and described above are presently preferred, it should be understood that these embodiments are offered by way of example only. For example, it is contemplated that the invention may be applied to systems in which more than one image manager is utilized. In another example, image handling system 10 may comprise a network involving more than one facility such that a workstation at a first facility may communicate with an image manager in a second (and remote) facility. Accordingly, the present invention is not limited to a particular embodiment, but extends to various modifications that nevertheless fall within the scope of the appended claims.

What is claimed is:

1. A method of providing a customized set of tools represented by icons in an image handling system, comprising:

receiving a selection of at least one tool represented by an icon, the at least one tool relating to access and navigation of information available in the image handling system;

storing the selection of the at least one tool in the customized set of tools in an image manager, wherein the customized set of tools is associated with a user identifier; and configuring an image workstation with the customized set of tools, the customized set of tools being selectively retrieved from the image manager in response to the user identifier being provided to the image workstation, wherein the customized set of tools is a subset of default commands for the image workstation, and wherein configuring the image workstation includes displaying at least one icon representative of the at least one tool at the image workstation.

2. The method of claim 1, wherein the image manager includes a picture archival and communications system (PACS) server and the image workstation includes a PACS workstation.

3. The method of claim 1, further comprising selectively retrieving an image data set from the image manager to be viewed by a user in accordance with the user identifier.

4. The method of claim 1, further comprising presenting a set of icons representing all available tools;

receiving a selection of one of the icons representing a tool;

including the selection of the one icon is a subset of tools associated with a user identifier; and repeating the receiving step a plurality of times as desired to configure the customized set of tools.

5. The method of claim 1, further comprising selectively saving the customized set of tools on the image manager.

6. The method of claim 1, wherein the customized set of tools includes a tool providing a link to at least one of preferred work files selected from a group including an all patients work file, an all exams work file, an all recent exams work file, an unread stat exams work file, an all unread exams work file, an unread by exam age work file, an unread by specialty work file, a priority exams work file, and an academic folders work file.

7. The method of claim 1, wherein the customized set of tools includes at least one of preferred image manipulation tools selected from a group including a magnify tool, a horizontal flip tool, a vertical flip tool, a pan tool, an image information tool, an invert grayscale tool, and an image mask tool.

8. A medical image handling system, comprising:

a medical imaging device configured to generate an image data set representative of a medical image;

an image manager coupled to the medical imaging device and configured to store a customized set of tools including a selection of at least one tool represented by an icon and the image data set, wherein the customized set of tools is associated with a user identifier; and an image workstation coupled to the image manager and including a graphical user interface (GUI), wherein the image workstation is configured to permit a user to select an interface tool from the GUI and store the selected interface tool in a customized set of tools in the image manager, and to retrieve the customized set of tools from the image manager for presentation on the image workstation as at least one icon when the user identifier is provided to the image workstation in a subsequent session on the image workstation.

9. The system of claim 8, wherein the image data set is in at least one of a DICOM and DEFF format.

10. The system of claim 8, further comprising a communications network coupled between the medical imaging device and the image manager, and coupled between the image manager and the image workstation.

11. The system of claim 9, wherein the customized set of tools includes a tool providing a link to preferred work files selected from a group including an all patients work file, an all exams work file, an all recent exams work file, an unread stat exams work file, an all unread exams work file, an unread by exam age work file, an unread by specialty work file, a priority exams work file, and an academic folders work file.

12. The system of claim 9, wherein the customized set of tools includes preferred image manipulation tools selected from a group including a magnify tool, a horizontal flip tool, a vertical flip tool, a pan tool, an image information tool, an invert grayscale tool, and an image mask tool.

13. The system of claim 9, wherein the image workstation is configured to permit the user to update the customized set of tools a plurality of times.

14. The system of claim 9, wherein the customized set of tools is selected from a group including tools providing links to quick access work files, quick access image navigation tools, and tools for changing preferred font and text size.

15. The system of claim 8, wherein the image manager includes a picture archival and communications system (PACS) server and the image workstation includes a PACS workstation.

16. An image handling system, comprising:

means for acquiring an image of a subject of interest;

means for representing the image in an image data set;

means for receiving a customized set of tools including a selection of at least one tool represented by an icon from a graphical user interface (GUI);

means for storing the customized set of tools communicated by an image workstation and the image data set communicated by the means for acquiring and representing, wherein the means for storing is coupled to the means for acquiring and representing;

means for selectively retrieving the customized set of tools and the image data set from the means for storing, wherein the image workstation automatically configures the GUI to incorporate the customized set of tools based in part on a user identifier information inputted to the image workstation, and wherein the customized set of tools comprises interface tools selected by a user relating to access and navigation within the image workstation; and means for displaying at least one icon representative of the customized set of tools at the image workstation.

17. The system of claim 16, wherein the image data set is in at least one of a DICOM and DEFF format.

18. The system of claim 16, further comprising means for networking coupled between the means for acquiring and the means for storing, and coupled between the means for storing and the image workstation.

19. The system of claim 16, wherein the user specifies the customized set of tools on the image workstation and the image workstation communicates the customized set of tools to the means for storing.

20. The system of claim 19, wherein the customized set of tools includes a tool providing a link to at least one of preferred work files selected from a group including an all patients work file, an all exams work file, an all recent exams work file, an unread stat exams work file, an all unread exams work file, an unread by exam age work file, an unread by specialty work file, a priority exams work file, and an academic folders work file.

21. The system of claim 19, wherein the customized set of tools includes at least one of preferred viewing tools selected from a group including a magnify tool, a horizontal flip tool, a vertical flip tool, a pan tool, an image information tool, an invert grayscale tool, and an image mask tool.

22. The system of claim 19, wherein the image workstation is configured to permit a plurality of changes to the customized set of tools.

23. The system of claim 19, wherein the means for storing selectively receives the customized set of tools in accordance with the user requesting storage of the customized set of tools.

24. The system of claim 16, wherein the means for storing includes a picture archival and communications system (PACS) server and the image workstation includes a PACS workstation.

25. A graphical user interface (GUI) for an image handling system, the image handling system including a workstation, the GUI comprising:

a first interface tool configured by a user of the image handling system to access data on the workstation; and a second interface tool configured by the user of the image handling system to navigate data on the workstation, wherein each of the first and second interface tools permits the user to access or navigate the data, respectively, without using a default access or navigation tool included in the GUI, the data being selected from a group including patient information and patient images, at least one of the first interface tool and the second interface tool being displayed as an icon on the workstation, and at least one of the first interface tool and the second interface tool being associated with a user identifier information.

26. The GUI of claim 25, wherein the first interface tool permits the user to access the data organized into work files, the work files selected from a group including an all patients work file, an all exams work file, an all recent exams work file, an unread stat exams work file, an all unread exams work file, an unread by exam age work file, an unread by specialty work file, a priority exams work file, and an academic folders work file.

27. The GUI of claim 25, wherein the second interface tool permits the user to navigate the data being displayed on the workstation, the second interface tool selected from a group including a magnify tool, a horizontal flip tool, a vertical flip tool, a pan tool, an image information tool, an invert grayscale tool, and an image mask tool.

28. The GUI of claim 25, further including a third interface tool configured by the user to customize the GUI on the workstation.

29. A method for configuring a graphical user interface (GUI) for a medical image handling system, the method comprising the steps of:

receiving an operator selection of an interface command from the GUI;

storing the interface command;

retrieving the interface command in accordance with a user identifier associated with the selected interface command; and customizing the GUI with the interface command, wherein the customizing step includes displaying an icon representative of the selected interface command on the GUI.

30. The method of claim 29, wherein the selecting step and the customizing step are performed on different workstations included in the medical image handling system.

* * * * *

UNITED STATES PATENT AND TRADEMARK OFFICE
CERTIFICATE OF CORRECTION

PATENT NO. : 6,411,836 B1
DATED : June 25, 2002
INVENTOR(S) : Alpesh P. Patel and Roland Lamer It is certified that error appears in the above-identified patent and that said Letters Patent is hereby corrected as shown below:

<u>Column 3,</u>
Line 39, after "manager 18," delete "Himage" and insert -- image --.

Signed and Sealed this

Twenty-eighth Day of January, 2003

JAMES E. ROGAN
*Director of the United States Patent and Trademark Office*